United States Patent
Lugade et al.

(10) Patent No.: US 7,867,774 B2
(45) Date of Patent: Jan. 11, 2011

(54) METHODS FOR ALTERING SURFACE CHARACTERISTICS OF MICROSPHERES

(75) Inventors: Ananda G. Lugade, Austin, TX (US); Kurt D. Hoffacker, Austin, TX (US)

(73) Assignee: Luminex Corporation, Austin, TX (US)

( * ) Notice: Subject to any disclaimer, the term of this patent is extended or adjusted under 35 U.S.C. 154(b) by 1157 days.

(21) Appl. No.: 11/247,943

(22) Filed: Oct. 11, 2005

(65) Prior Publication Data

US 2006/0078997 A1 Apr. 13, 2006

Related U.S. Application Data

(60) Provisional application No. 60/618,338, filed on Oct. 12, 2004.

(51) Int. Cl.
*G01N 21/75* (2006.01)
*G01N 37/00* (2006.01)
*A61K 9/16* (2006.01)

(52) U.S. Cl. .................. 436/166; 436/56; 424/490; 536/53; 536/55.3; 435/395; 435/396

(58) Field of Classification Search .................. None
See application file for complete search history.

(56) References Cited

U.S. PATENT DOCUMENTS

| | | | |
|---|---|---|---|
| 2,657,205 | A | 10/1953 | Heyna et al. |
| 4,935,147 | A | 6/1990 | Ullman et al. |
| 5,414,135 | A | 5/1995 | Snow et al. |
| 5,674,699 | A | 10/1997 | Saunders et al. |
| 5,736,330 | A | 4/1998 | Fulton |
| 5,763,203 | A | 6/1998 | Ugelstad et al. |
| 5,981,180 | A | 11/1999 | Chandler et al. |

(Continued)

FOREIGN PATENT DOCUMENTS

DE 960534 3/1957

(Continued)

OTHER PUBLICATIONS

Kaminski, "Triazine-Based Condensing Reagents", Peptide Science, vol. 55, No. 2, pp. 140-164 (2000) (Kaminski).*

(Continued)

*Primary Examiner*—Krishnan S Menon
*Assistant Examiner*—Dirk Bass
(74) *Attorney, Agent, or Firm*—Charles D. Huston; Mollie E. Lettang; Daffer McDaniel, LLP

(57) ABSTRACT

Various methods for altering surface characteristics of a microsphere are provided. One method includes coupling an enolic acid to the microsphere to modify the surface characteristics of the microsphere. The surface characteristics may include charge density and/or pKa. A reagent can be coupled to the microsphere via the enolic acid. The reagent may include a biomolecule. The modified surface characteristics may increase a stability of the reagent when the reagent is coupled to the microsphere. The modified surface characteristics may also improve performance of an assay carried out with the microsphere. Another embodiment relates to a microsphere that includes an enolic acid coupled to a polymer core of the microsphere such that the enolic acid modifies surface characteristics of the microsphere. A reagent can be coupled to the microsphere via the enolic acid.

20 Claims, 1 Drawing Sheet

U.S. PATENT DOCUMENTS

| | | | |
|---|---|---|---|
| 6,008,406 | A | 12/1999 | Stolowitz |
| 6,046,807 | A | 4/2000 | Chandler |
| 6,057,107 | A | 5/2000 | Fulton |
| 6,075,126 | A | 6/2000 | Stolowitz et al. |
| 6,124,471 | A | 9/2000 | Stolowitz et al. |
| 6,139,800 | A | 10/2000 | Chandler |
| 6,146,833 | A | 11/2000 | Milton |
| 6,268,222 | B1 | 7/2001 | Chandler et al. |
| 6,366,354 | B1 | 4/2002 | Chandler |
| 6,411,904 | B1 | 6/2002 | Chandler |
| 6,449,562 | B1 | 9/2002 | Chandler et al. |
| 6,462,179 | B1 | 10/2002 | Stolowitz et al. |
| 6,514,295 | B1 | 2/2003 | Chandler et al. |
| 6,524,793 | B1 | 2/2003 | Chandler et al. |
| 6,602,692 | B1 | 8/2003 | Glusenkamp et al. |
| 6,630,577 | B2 | 10/2003 | Stolowitz et al. |
| 6,632,526 | B1 | 10/2003 | Chandler et al. |
| 6,656,876 | B1 | 12/2003 | Åberg et al. |
| 2003/0028981 | A1 | 2/2003 | Chandler et al. |
| 2004/0039201 | A1 | 2/2004 | Lugade et al. |
| 2004/0087032 | A1 | 5/2004 | Chandler et al. |
| 2005/0118199 | A1* | 6/2005 | Esser et al. .............. 424/244.1 |

FOREIGN PATENT DOCUMENTS

| | | |
|---|---|---|
| EP | 0230768 | 3/1992 |
| JP | 8092294 | 4/1996 |
| WO | 99/67228 | 12/1999 |
| WO | 02/40698 | 5/2002 |

OTHER PUBLICATIONS

International Search Report, PCT/US2005/036264, mailed Jan. 15, 2007.

Pyzhov et al., "Chemical Heterocyclic Connections," © VINITI 1982, 8 pages.

Fulton et al., "Advanced multiplexed analysis with the FlowMetrix™ system," Clinical Chemistry, vol. 43, No. 9, 1997, pp. 1749-1756.

Adams et al., "Far-infrared Reflectance Spectra of Some Hexachlorotellurates and Other Hexachlorometallates," J. Chem. Soc. (A), 1971, pp. 878-879.

Ahne et al., "Partielle Aminolyse von 2,4,6-Triallyloxy-s-triazin. Teil 2: Herstellung von N,N'-Bis[4,6-diallyloxy-2-s-triazinyl]diaminoalkanen," Synthesis Communications, Mar. 1975, pp. 184-186.

Bartels-Keith et al., "A Synthesis of Stipitatic Acid," J. Chem. Soc., 1951, pp. 2352-2356.

Bellus, "[2+2] Cycloadditions of Tetraalkoxyethylenes with Ketenes: a General Route to 2-Substituted 1-Hydroxycyclobut-1-ene-3,4-diones," Journal of the American Chemical Society, vol. 100, No. 25, Dec. 1978, pp. 8026-8028.

Belogi et al., "Polystyrylboronic acid as a reusable polymeric support for oligosaccharide synthesis," Tetrahedron Letters, No. 41, 2000, pp. 6965-6968.

Hermanson, *Bioconjugate Techniques*, © Elsevier 1996, Chapters 1-9.

Hermanson, *Bioconjugate Techniques*, © Elsevier 1996, Chapters 10-17.

Blixt et al., "Enzymatic glycosylation of reducing oligosaccharides linked to a solid phase or a lipid via a cleavable squarate linker," Carbohydrate Research, vol. 319, 1999, pp. 80-91.

Cole et al., "Toxin from Fusarium moniliforme: Effects on Plants and Animals," Science, vol. 179, 1973, pp. 1324-1326.

Frey et al., "Grafting Protein Ligand Monolayers onto the Surface of Microparticles for Probing the Accessibility of Cell Surface Receptors," Bioconjugate Chem., vol. 10, 1999, pp. 562-571.

James et al., "Novel Photoinduced Electron-transfer Sensor for Saccharides based on the Interaction of Boronic Acid and Amine," J. Chem. Soc., Chem. Commun., 1994, pp. 477-478.

Konek et al., "Interfacial Acidities, Charge Densities, Potentials, and Energies of Carboxylic Acid-Functionalized Silica/Water Interfaces Determined by Second Harmonic Generation," J. Am. Chem. Soc., vol. 124, 2004, pp. 11754-11755.

Kunishima et al., "Synthesis and Characterization of 4-(4,6-Dimethoxy-1,3,5-triazin-2-yl)-4-methylmorpholinium Chloride," Tetrahedron Letters, No. 40, 1999, pp. 5327-5330.

Law et al., "Squaraine Chemistry. Synthesis, Characterization, and Optical Properties of a Class of Novel Unsymmetrical Squaraines: [4-(Dimethylamino)phenyl](4'-methoxyphenyl)squaraine and Its Derivatives," J. Org. Chem., vol. 57, 1992, pp. 3278-3286.

Kettman et al., "Classification and Properties of 64 Multiplexed Microsphere Sets," Cytometry, vol. 33, 1998, pp. 234-243.

Meier et al., "Bis(stilbenyl)squaraines—Novel Pigments with Extended Conjugation," Tetrahedron Letters, vol. 37, No. 8, 1996, pp. 1191-1194.

Roberts et al., "Chemistry for peptide and protein PEGylation," Advanced Drug Delivery Reviews, vol. 54, 2002, pp. 459-476.

Salvino et al., "Polymer-Supported Tetrafluorophenol: A New Activated Resin for Chemical Library Synthesis," J. Comb. Chem., vol. 2, 2000, pp. 691-697.

Schmidt et al., "Die preparative Chemie der Cyclobutendione; I. Synthese con Cyclobutendion und dessen Alkyl-, Alkenyl- und Aryl-Derivaten," © Georg Thieme Publishers 1978, pp. 1-22.

Venkataraman et al., "Cyanuric Chloride: A Useful Reagent for Converting Carboxylic Acids Into Chlorides, Esters, Amides and Peptides," Tetrahedron Letters, No. 32, 1979, pp. 3037-3040.

Yoon et al., "Fluorescent Chemosensors of Carbohydrates. A Means of Chemically Communicating the Binding of Polyols in Water Based on Chelation-Enhanced Quenching," J. Am. Chem. Soc., vol. 114, 1992, pp. 5874-5875.

Valuev et al., "Chemical modification of polymers with physiologically active species using water-soluble carbodiimides," Biomaterials, vol. 19, 1998, pp. 41-43.

Renbaum et al., "Design of Polymeric Immunomicrospheres for Cell Labelling and Cell Separation," The British Polymer Journal, vol. 10, Dec. 1978, pp. 275-280.

Medvedkin et al., "p-Sulfotetrafluorophenyl Hydrophilic Active Esters of Amino Acids in Peptide Synthesis," Bioorg. Khirn., vol. 21, No. 9, 1995, pp. 684-690.

Kashkin et al., "Fluorine-Containing Hydroxyalkylamino-1,3,5-Triazines," Zhurnal Organicheskoi Khimii, vol. 12, No. 9, Sep. 1976, pp. 2030-2033.

Bergseid et al., "Small Molecule-Based Chemical Affinity System for the Purification of Proteins," BioTechniques, vol. 29, No. 5, 2000, pp. 1126-1133.

Sprenger et al., "Cyclobutenediylium Dyes," Angew. Chem. Internat. Edit., vol. 7, No. 7, 1968, pp. 530-535.

Martin et al., "Einfache Sythesen für Amino-aroxy-1,3,5-triazine," Journal f. prakt. Chemie. Band, vol. 323, No. 4, 1981, pp. 694-699.

McDade et al., "True Multiplexed Analysis by Computer-Enhanced Flow Cytometry," Medical Device & Diagnostic Industry Magazine, Apr. 1997, 5 pages.

*Methods in Cell Biology*, vol. 42, © Academic Press 1994, pp. 575-595.

Nikiforov et al., "Genetic Bit Analysis: a solid phase method for typing single nucleotide polymorphisms," Nucleic Acids Research, vol. 22, No. 20, 1994, pp. 4167-4175.

Upson, "Reactive Functional Latex Polymers," Journal of Polymer Science: Polymer Symposium, vol. 72, 1985, pp. 45-54.

Margel et al., "Polychloromethylstyrene Microspheres: Synthesis and Characterization," Journal of Polymer Science: Part A: Polymer Chemistry, vol. 29, 1991, pp. 347-355.

Margel et al., Novel Effective Immunoadsorbents Based on Agarose-Polyaldhyde Microsphere Beads: Synthesis and Affinity Chromatography, Analytical Biochemistry, vol. 128, 1983, pp. 342-350.

Ugelstad et al., "Swelling of Oligomer-Polymer Particles, New Methods of Preparation of Emulsions and Polymer Dispersions," Advances in Colloid and Interface Science, vol. 13, 1980, pp. 101-140.

Dennis et al., "1,3-Dipolar Character of Six-membered Aromatic Rings. Part XXV. 5-Aryl-1-methyl-3-oxidopyridiniums," J. Chem. Soc., 1976, pp. 2329-2334.

Arshady, "Microspheres for biomedical applications: preparation of reactive and labelled microspheres," Biomaterials, vol. 14, No. 1, 1993, pp. 5-15.

Ugelstad et al., "Absorption of Low Molecular Weight Compounds in Aqueous Dispersions of Polymer-Oligomer Particles," Makromol. Chem., vol. 180, 1979, pp. 737-744.

Chan et al., "Inactivation of Bovine Thrombin by Water-Soluble Carbodiimides: The Essential Carboxyl Group has a $pK_a$ of 5.51," Biochemical and Biophysical Research Communication, vol. 151, No. 2, 1988, pp. 709-716.

Cronin et al., "An Improved Procedure for the Large Scale Preparation of 2-chloro-4,6-dimethoxy-1,3,5-triazine," Synthetic Communication, vol. 26, No. 18, 1996, pp. 3491-3494.

Gauger et al., "Kondensationsprodukte der Quadratsäure mit primären and sekundären Aminen," Chem. Ber., vol. 103, 1970, pp. 2696-2706.

Uemura et al., "Syntheses and Thermal Properties of New Liquid Crystalline Materials Involving Tropolone," Mol. Cryst. Liq. Cryst., vol. 95, 1983, pp. 287-297.

Gilles et al., "Stability of Water-Soluble Carbodiimides in Aqueous Solution," Analytical Biochemistry, vol. 184, 1990, pp. 244-248.

Renbaum et al., "Synthesis and Reactions of Hydrophilic Functional Microspheres for Immunological Studies," J. Macromol. Sci.-Chem., vol. A13, No. 5, 1979, pp. 603-632.

*The Chemistry of Synthetic Dyes*, vol. VI, © Academic Press 1972, pp. 1-108.

*Synthesis and Separations Using Functional Polymers*, © John Wiley 1988, pp. 44-113.

* cited by examiner

METHODS FOR ALTERING SURFACE CHARACTERISTICS OF MICROSPHERES

PRIORITY CLAIM

This application claims priority to U.S. Provisional Application No. 60/618,338 entitled "Methods for Altering Surface Characteristics of Microspheres," filed Oct. 12, 2004, which is incorporated by reference as if fully set forth herein.

BACKGROUND OF THE INVENTION

1. Field of the Invention

This invention generally relates to methods for altering surface characteristics of microspheres. Certain embodiments include coupling an enolic acid to the microsphere to modify the surface characteristics of the microsphere such that a reagent can be coupled to the microsphere via the enolic acid.

2. Description of the Related Art

The following descriptions and examples are not admitted to be prior art by virtue of their inclusion within this section.

Spectroscopic techniques are widely employed in the analysis of chemical and biological systems. Most often, these techniques involve measuring the absorption or emission of electromagnetic radiation by the material of interest. One such application is in the field of microarrays, which is a technology exploited by a large number of disciplines including the combinatorial chemistry and biological assay industries. One company, Luminex Corporation of Austin, Tex., has developed a system in which biological assays are performed on the surface of variously colored fluorescent microspheres. One example of such a system is illustrated in U.S. Pat. No. 5,981,180 to Chandler et al., which is incorporated by reference as if fully set forth herein. In such a fluid flow device, microspheres are interrogated by laser excitation and fluorescence detection of each individual microsphere as it passes at relatively high speed through a detection zone. Measurement data generated by such a system may be easily exported to a database for further analysis.

Assays based on fluorescent microspheres for multiplexed analysis have been also reported by several groups and individuals as described by Fulton et al., *Clin. Chem.*, 1997, 43, 1749-1756; Kettman et al., *Cytometry*, 1998, 33, 234-243; McDade et al., *Med. Dev. Diag. Indust.*, 1997, 19(4), 75-82; McHugh, *Methods Cell Biol.*, 1994, 42, 575-595; and Nikiforov et al., *Nucleic Acid Res.*, 1994, 22, 4167-4175; and U.S. Pat. No. 5,736,330 to Fulton, U.S. Pat. No. 6,046,807 to Chandler, U.S. Pat. No. 6,057,107 to Fulton, U.S. Pat. No. 6,139,800 to Chandler, U.S. Pat. No. 6,268,222 to Chandler et al., U.S. Pat. No. 6,366,354 to Chandler, U.S. Pat. No. 6,411,904 to Chandler, and U.S. Pat. No. 6,449,562 to Chandler et al., which are incorporated by reference as if fully set forth herein.

In the above-mentioned systems, fluorescent dyes are absorbed into the microspheres and/or bound to the surface of the microspheres. The dyes are chosen based on their ability to emit light in the wavelength of a chosen detection window of the system. Further, the detection windows are spaced apart by a number of wavelengths, and the dyes are designed to minimize the overlap of a dye's fluorescent signal within adjacent detection windows. By employing two detection windows and two dyes, each at 10 different concentrations, there would thus be 100 fluorescently distinguishable microsphere sets.

In the last three decades, advancements in the fields of affinity chromatography, solid-phase synthesis, and immobilization of bio-macromolecules, such as proteins, oligonucleotides and the like, have led to microsphere-based biomedical applications. For example, one or more biomolecules may be bound to the surface of microspheres. The one or more biomolecules are selected based on the specific assay to be carried out. For example, one population of microspheres may include different subsets of microspheres, each coupled to a different antigen. The subsets may be combined with a sample, and the assay may be performed to determine which antibodies are present in the sample. The biomolecule(s) that are bound to the microspheres may include any biomolecules known in the art.

The immobilization of biomolecules or any other such entities can be achieved by coupling by (a) ionic interactions; (b) adsorption; (c) complexation (e.g. "metal-coordination" mediated coupling); and (d) covalent bond formation between active/stable reactive groups on the surface and specific functional groups on the entity to be immobilized. For example, particles (e.g., micro- and nano-spheres; nanotubes; metal particles including one or more metals with any size, shape, or composition; semiconductor particles; molecularly imprinted polymers (MIPS); magnetic particles; and other dyed materials) and microtiter plates are common solid matrices in many immobilization systems. Preparing and maintaining the active, functionalized surface of the solids are important to assure immobilization of biological material for development of a sufficiently sensitive assay. Current procedures for immobilization of biomolecules on solid surfaces generally involve reactions of activated carboxyl, amino-, hydroxyl- or thiol-groups on the solid surfaces with the biomolecules. After activation of, or introduction of a functionalized spacer to, these groups, the activated groups provide sites on the solid surface for direct attachment of the biomolecules.

Currently used groups for providing direct attachment sites, however, have a number of disadvantages. For example, most of these functional groups (such as N-hydroxysuccinimide (NHS) esters, isothiocyanates, etc.) are prone to hydrolysis in an aqueous environment and become non-reactive (i.e., chemically inactive) in a matter of less than an hour. Therefore, such functional groups may undesirably exhibit time-dependent variations in the quantity, repeatability, and uniformity with which biomolecules may be attached to the surface of solids using these functional groups.

Reactive or functionalized microspheres are conventionally produced via copolymerization of suitably functionalized monomers or via chemical modification of preformed microspheres. Post-functionalization is a popular method for preparing reactive particles as earlier described by Upson, (*J. Polym. Sci., Polym. Symp.*, 1985, 72, 45, which is incorporated by reference as if fully set forth herein.

More recent work on the production and evaluation of a variety of tailor-made particles has been reported by several groups including Margel, et al., (*J. Polym. Sci.*, 1991, A-29, 347-355; *Anal. Biochem.*, 1981, 128, 342-350), Ugelstad et al., (*Makromol. Chem.*, 1979, 180, 737-744; *Adv. Colloid Interface Sci.*, 1980, 13, 102-140), and Rembaum et al. (*Br. Polym. J.*, 1978, 10, 275-280; *J. Macromol. Sci. Chem.*, 1979, A-13, 603-632), which are incorporated by reference as if fully set forth herein. A review by R. Arshady, *Biomaterials*, 1993, 14, 5-15, which is also incorporated by reference as if fully set forth herein, describes the synthesis and physicochemical properties of reactive and labeled microspheres.

Fray et al., *Bioconjugate Chem.*, 1999, 10, 562-571, which is incorporated by reference as if fully set forth herein, have reported a strategy in which particles are pre-activated with hydrolysis-resistant aldehyde functional groups, but low reaction yields of less than 8% have been observed with these microspheres. U.S. Pat. No. 6,146,833 to Milton, which is incorporated by reference as if fully set forth herein, describes a reaction between an acyl fluoride activated polymer-surface and an amino derivatized biomolecule at room temperature. The use of fluorophenyl resins in the solid phase synthesis of amides, peptides, hydroxamic acids, amines, urethanes, carbonates, sulfonamides, and alpha-substituted carbonyl compounds has been described in International Publication No. WO 99/67228 to Clerc et al., which is incorporated by reference as if fully set forth herein.

Medvedkin et al., *Bioorg. Khirn.*, 1995, 21(9), 684-690, which is incorporated by reference as if fully set forth herein, illustrates using sulfo-tetrafluorophenyl activated esters in peptide synthesis and demonstrates their reactivity combined with good stability under aqueous storage conditions. Apparently, the pre-activation of a polystyrene surface with this reagent has not yet been reported.

Hoechst, in German Patent No. DE 960,534 to Heyna et al., which is incorporated by reference as if fully set forth herein, claimed the use of reactive vinyl sulfone (VS)-modified dyes for dyeing of cellulose and wool fibers in 1950. A review by Siegel provides a complete account of reactive dyes based on VS and its protected 2-sulfatoethyl and 2-thiosulfatoethyl sulfones (E. Siegel in *The Chemistry of Synthetic Dyes*, Vol. VI, (Ed. K Venkataraman); 2-108, Academic Press, 1972, which is incorporated by reference as if fully set forth herein). U.S. Pat. No. 5,414,135 to Snow et al., which is incorporated by reference as if fully set forth herein, describes modification of proteins with PEG-supported VS.

The most frequently used method to immobilize biomolecules (such as oligonucleotides, proteins, and carbohydrates) onto fluorescent microspheres is by activating carboxy groups present on the surface of the microspheres. The activation requires excess N-ethyl-N'-(3-dimethylaminopropyl)carbodiimide (EDC) and a coupling pH of 4 to 6. The reaction between the carbodiimide and carboxyl functional groups forms an activated O-acylurea derivative reaction intermediate. A subsequent nucleophilic attack of the reaction intermediate by the primary nitrogen of the amino-groups of the biomolecule being attached to the microspheres releases the substituted urea and produces an amide linkage between the reaction intermediate and the biomolecule.

There are, however, a number of disadvantages to such activation of the carboxy groups. For example, the reaction intermediate has an extremely short half-life and rapidly undergoes hydrolysis or rearranges to produce the N-acylurea adduct. In addition, the optimum pH for the formation of O-acylurea is about 4-5. However, the primary amino group of the nucleophile is predominantly protonated at a pH of about 4-5 and is thus mostly unreactive. These limitations of the reaction intermediate can severely restrict coupling yields of biomolecules to microspheres. Furthermore, at low pH, nucleic acid bases of a biomolecule may undergo intensive protonation. Such protonation induces DNA melting that exposes the hydrophobic core of the helix thereby facilitating nonspecific hydrophobic interactions of the helix with the solid matrix of the micro spheres.

Despite these drawbacks, EDC-mediated coupling is currently the major mode of covalent immobilization of biomolecules to solid surfaces as described by Hermanson, G. T., in *Bioconjugate Techniques*, Academic Press, NY, 1996; Frey, A. et al., *Bioconjugate Chem.*, 1999, 10, 562-571; Gilles, M. A. et al., *Anal. Biochem.*, 1990, 184, 244-248; Chan V. W. F. et al., *Biochem. Biophys. Res. Communications*, 1988, 151 (2), 709-716; and Valuev, I. L. et al., *Biomaterials*, 1998, 19, 41-43, which are all incorporated by reference as if fully set forth herein.

For combinatorial libraries, building blocks such as malonic acids, dihydroxy benzoic acid, hydroxy phenyl acetic acid, pyroline carboxylic acids, bromodihydroxy benzoic acids, 3-oxo-1-indancarboxylic acid, 3-nitrophenyl acetic acid, and 3,4-difluoro benzoic acid have been reported by, for example, Lin, R. et al., in *J. Am. Chem. Soc.*, 2002, 124, 7678-7680, which is incorporated by reference as if fully set forth herein.

Some molecules that can be incorporated into polymers to modify the surface characteristics of the polymers have been reported and are shown below.

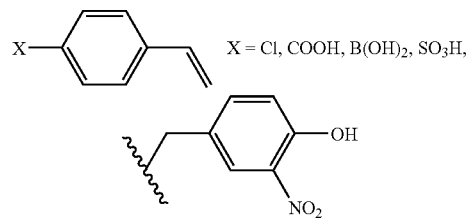

Organic reactions using polymer supported catalysts, reagents or substrates are known as described by, for example, Hodge, P. in "Synthesis and separations using functional polymers," Editors, Sherrington, D. C. & Hodge, P., 1988, John Wiley, 44-113, which is incorporated by reference as if fully set forth herein.

Polymer supported phenolic compounds are known. For example, polymer supported tetrafluoro phenol is now used as an activated resin for chemical library synthesis as described by Salvino, J. M. et al., *J. Comb. Chem.*, 2000, 2, 691-699, which is incorporated by reference as if fully set forth herein.

Boronic acid is routinely incorporated into synthetic receptors for the complexation of saccharides and other guests that possess 1,2 and 1,3 diol functionality, as described by Czarnik, A. W. et al., *J. Am. Chem. Soc.* 1992, 114, 5874, Shinkai, S. J., *J. Chem. Soc. Chem. Commun.*, 1994, 477, and Geert-Jan Boons et al., *Tetrahedron Lett.*, 200, 41, 6965, which are incorporated by reference as if fully set forth herein. Boronic acids have also been incorporated into a chemical affinity system for the purification of proteins, as described by Bergseid, M. et al., in *Biotechniques*, 2000, 29, 1126, which is incorporated by reference as if fully set forth herein. The use of various boronic acids to link two entities together has been disclosed in U.S. Pat. No. 6,008,406 to Stolowitz, U.S. Pat. No. 6,075,126 to Stolowitz et al., U.S. Pat. No. 6,124,471 to Stolowitz et al., U.S. Pat. No. 6,462,179 to Stolowitz et al., and U.S. Pat. No. 6,630,577 to Stolowitz et al., which are incorporated by reference as if fully set forth herein.

Acidic functional groups have also been added to glass surfaces as described by, for example, Geiger, F. M. et al., *J. Am. Chem. Soc.*, 2004, 126, 11754, which is incorporated by reference as if fully set forth herein.

Accordingly, it would be advantageous to develop a method for altering the surface characteristics of a microsphere without one or more of the disadvantages described above such as time-dependent variations in the attachment of biomolecules to the surface of microspheres due to hydrolysis of the functional groups used to attach the biomolecules.

SUMMARY OF THE INVENTION

The following description of various method, microsphere, and kit embodiments is not to be construed in any way as limiting the subject matter of the appended claims.

One embodiment relates to a method for altering surface characteristics of a microsphere. The method includes coupling an enolic acid to the microsphere to modify the surface characteristics of the microsphere. The enolic acid may include one or more enolic acid molecules coupled to different locations on the microsphere. A reagent can be coupled to the microsphere via the enolic acid. In other embodiments, the enolic acid may be replaced with an enolic acid derivative or a mixed functional group. In further embodiments, the enolic acid may be more generally represented as an ionizable polar group that is in conjugation with a chemical group. The chemical group may include, for example, a sulfone group or a carbonyl group.

In one embodiment, the enolic acid contains at least one hydrophilic group. In another embodiment, the enolic acid may include a deltic, squaric, croconic, or rhodizonic acid, or other homolog. In a different embodiment, the enolic acid may include 5-substituted hydroxy tropolone. In other embodiments, the enolic acid may include a cyanuric acid or a cyanuric acid derivative. In alternative embodiments, the enolic acid may include dimethoxy triazine methylmorpholine modified to contain hydrophilic groups. In a further embodiment, the enolic acid may include a mixed functional group. The mixed functional group may include a boronic acid or a boronic acid derivative. In some embodiments, the enolic acid may include a silicic acid or a silicic acid derivative.

In an embodiment, coupling the enolic acid to the microsphere may include copolymerizing a monomer containing a vinyl group and the enolic acid with a different monomer to form the microsphere having the modified surface characteristics. In a different embodiment, coupling the enolic acid to the microsphere may include attaching the enolic acid to a surface of the microsphere.

The modified surface characteristics may increase a stability of the reagent when the reagent is coupled to the microsphere. The modified surface characteristics may also improve performance of an assay carried out with the microsphere. The reagent may include, for example, a biomolecule.

The surface characteristics may include charge density. In addition, or alternatively, the surface characteristics may include pKa. Each of the embodiments of the method described above may include any other step(s) described herein. In addition, the method may obviously include altering the surface characteristics as described above of multiple microspheres simultaneously (i.e., in the same steps).

Another embodiment relates to a microsphere that includes an enolic acid coupled to a polymer core of the microsphere such that the enolic acid modifies surface characteristics of the microsphere. The enolic acid may include one or more enolic acid molecules coupled to different locations on the microsphere. A reagent can be coupled to the microsphere via the enolic acid. In other embodiments, the enolic acid may be replaced with an enolic acid derivative or a mixed functional group. In further embodiments, the enolic acid may be more generally represented as an ionizable polar group that is in conjugation with a chemical group. The chemical group may include a sulfone group or a carbonyl group.

In one embodiment, the enolic acid contains at least one hydrophilic group. In another embodiment, the enolic acid may include a deltic, squaric, croconic, or rhodizonic acid or other homolog. In a different embodiment, the enolic acid may include 5-substituted hydroxy tropolone. In other embodiments, the enolic acid may include a cyanuric acid or a cyanuric acid derivative. In a further embodiment, the enolic acid may include dimethoxy triazine methylmorpholine modified to contain hydrophilic groups. In alternative embodiments, the enolic acid may include a mixed functional group. The mixed functional group may include a boronic acid or a boronic acid derivative. In different embodiments, the enolic acid may include a silicic acid or a silicic acid derivative.

In one embodiment, the enolic acid may be coupled to the polymer core via copolymerization using a monomer containing a vinyl group and the enolic acid with a different monomer. In a different embodiment, the enolic acid may be coupled to the polymer core via attachment of the enolic acid to a surface of the polymer core.

The modified surface characteristics may increase a stability of the reagent when the reagent is coupled to the microsphere. The modified surface characteristics may also improve performance of an assay carried out with the microsphere. The reagent may be a biomolecule. The surface characteristics may include charge density. In addition, the surface characteristics may include pKa. Each of the embodiments of the microsphere may be further configured, composed, and/or formed as described herein.

An additional embodiment relates to a kit. The kit includes microspheres. The kit also includes an activating reagent containing an enolic acid. In addition, the kit includes one or more chemicals, one or more devices, or some combination thereof that can be used to couple the enolic acid to a polymer core of the microsphere such that the enolic acid modifies surface characteristics of the microspheres. One or more reagents can be coupled to the microspheres via the enolic acid.

The kit and these elements of the kit may be further configured as described herein. For example, in some embodiments, the enolic acid may be replaced with an enolic acid derivative or a mixed functional group. In further embodiments, the enolic acid may be more generally represented as an ionizable polar group that is in conjugation with a chemical group. The chemical group may include, for example, a sulfone group or a carbonyl group.

BRIEF DESCRIPTION OF THE DRAWINGS

Other objects and advantages of the invention will become apparent upon reading the following detailed description and upon reference to the accompanying drawings in which.

Figure 1:
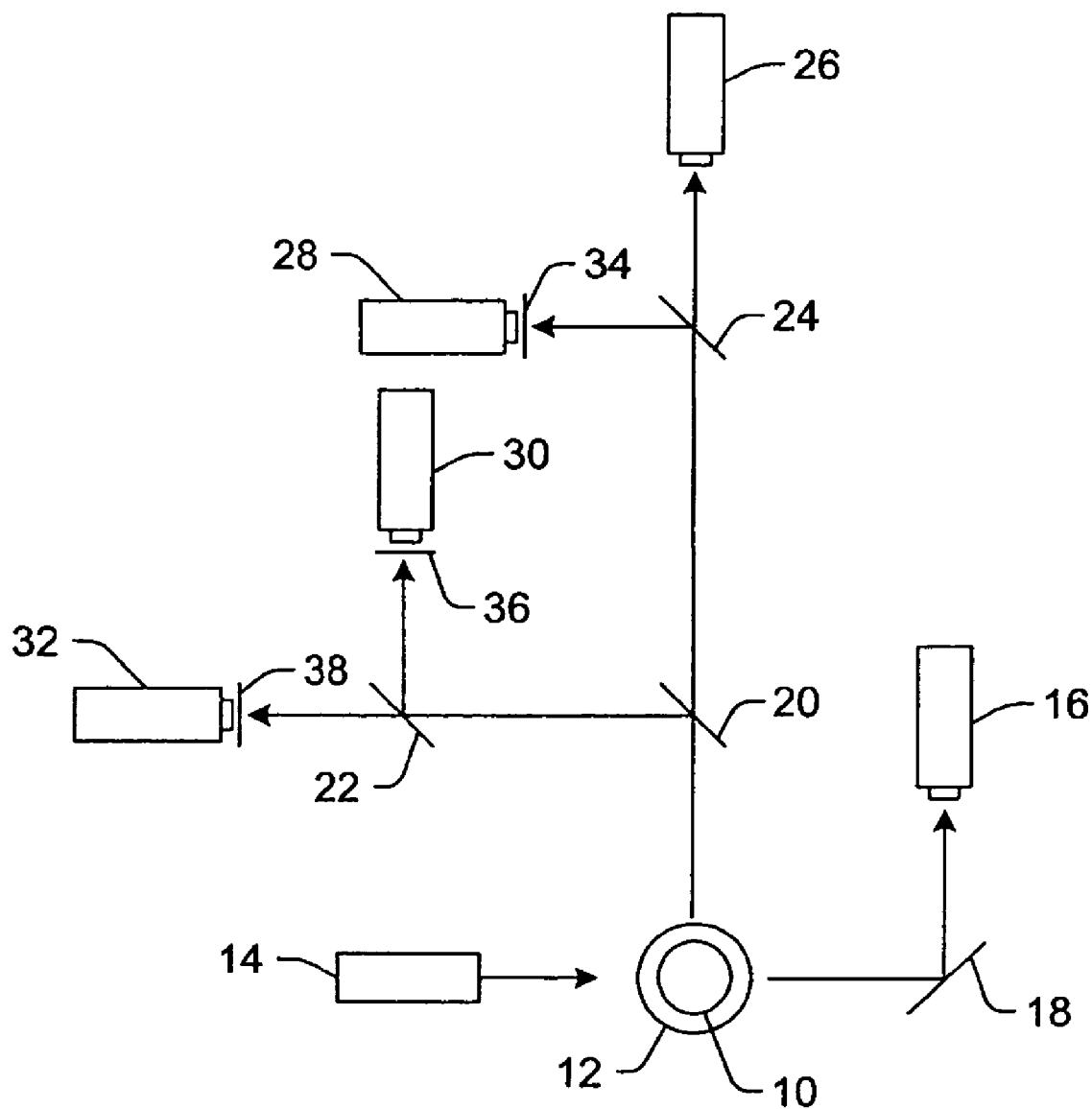
FIG. 1 is a schematic diagram illustrating one example of a measurement system that may be used to perform experiments using embodiments of microspheres described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The terms "microspheres," "particles," and "beads" are used interchangeably herein to refer to discrete solid substances having any suitable size and shape known in the art and having a surface to which one or more surface modifiers described herein may be coupled.

As used herein, the term "surface modifier" generally refers to one or more molecules that can be coupled to or otherwise located on a surface of a microsphere and that can alter a characteristic of the surface of the microsphere.

As used herein, the term "reagent" generally refers to a molecule that is coupled to a microsphere such that the reagent can react with an analyte during an assay or other experiment performed using the microsphere. Examples of appropriate reagents include, but are not limited to, biomolecules such as proteins, nucleotides, oligonucleotides, enzymes, antigens, antibodies, or any other molecule involved in or related to biological functioning of a human, animal, plant, etc., drug candidates, and dyes.

Methods of forming microspheres having surfaces (e.g., polystyrene surfaces) with unusual acidity are generally described herein. For example, methods are described herein for coupling one or more surface modifiers such as enolic acid derivatives to microspheres. In one embodiment, a method for altering surface characteristics of a microsphere includes coupling an enolic acid to the microsphere to modify the surface characteristics of the microsphere. A reagent can be coupled to the microsphere via the enolic acid. Although the method embodiments are described herein with respect to a microsphere, it is to be understood that an enolic acid may be coupled to multiple microsphere simultaneously (i.e., in the same step or steps of the method).

The surface properties of polymeric microspheres play an important role in many applications involving a wide spectrum of bioassays. For example, the surface characteristics of microspheres determine if and which reagents can be attached to the microspheres. In addition, the surface characteristics of microspheres may determine the amount, predictability, repeatability, uniformity, etc. in which reagents can be coupled to the microspheres. In most commercially available microspheres, functional monomers terminating in COOH or $SO_3H$ groups have been used to form the activated (or functionalized) surface of the polymer core of the microspheres. Acidic microsphere surfaces are currently produced using groups such as carboxyl, sulfoxide, hydroxide, boronic acid and silicic acid.

The methods described herein, however, include modifying microsphere surfaces using surface modifiers such as ionizable polar groups in conjugation with a chemical group such as sulfone or carbonyl groups. For example, microsphere surfaces, as described herein, may be charged (or functionalized) with groups including, but not limited to, carbonyl and OH on adjacent carbon atoms and in conjugation, carbonyl and OH separated by a double bond or by another conjugating link, sulfone and OH in conjugation, carbonyl and COOH, sulfone and COOH, boronic acid and OH, and silicic acid and COOH. In contrast, acids currently used as surface modifiers include ionizable groups located on a carbon, boron, sulfur or silicon atom.

Enolic acids contain oxo and hydroxyl groups located on different atoms, which are separated by one or more double bonds. Depending on the pH of the solution in which microspheres are disposed, enolic acid groups located on the surface of the microspheres can be ionized and can influence the surface charge (e.g., charge density) of the microsphere and the interfacial charge (i.e. the charge at the interface between the aqueous solution and the microsphere surface). In other words, the enolic acid may be coupled to the microsphere to modify surface characteristics such as surface charge and interfacial charge of the microsphere. These changes in the surface charge and the interfacial charge, in turn, can control chemical binding (or coupling) to the surface of the microspheres and particularly coupling between reagents such as biomolecules and the solid surface. The reagent(s) may also be coupled to the microsphere via the enolic acid.

The methods described herein can be performed using the following enolic acids, enolic acid derivatives and mixed functional groups. For example, the method described herein can be performed using enolic acids such as squaric, cyanuric, and boronic acids, as well as seven membered hydroxytropolone and trialkyl silyl compounds.

U.S. Patent Application Publication No. 2004/0039201 to Lugade et al., which is incorporated by reference as if fully set forth herein, describes the use of squaric acid fluoride as a preactivated enolic acid fluoride for the covalent coupling of the amino groups of biomolecules. The methods described herein utilize several enolic acids and their derivatives in developing additional reagents for an array of biomedical applications.

In one embodiment, the methods described herein may be performed using enolic acids such as squaric acid or a derivative thereof. Squaric acid is a substantially strong, dibasic acid having a pKa in the range of about 2 to about 3.5. By transferring two protons, squaric acid can generate a squarate dianion, which is a relatively rigid and delocalized planar aromatic dianion capable of acting as a powerful acceptor of hydrogen bonds. Other homologues of this acid such as deltic, croconic, and rhodizonic acid can be used in the method embodiments described herein. Surfaces with appended squaric acid esters (made from an amine containing surface) have been used to conjugate with amine containing molecules. Examples of methods involving squaric acids are described by Blixt, O. et al., in "Enymatic glycosoylation of reducing oligosaccharides linked to a solid phase or a lipid via a cleavable squarate linker," *Carbohydrate Research*, 1999, 319, 80-91, and U.S. Pat. No. 6,602,692 to Glusenkamp et al. and U.S. Pat. No. 6,656,876 to Aberg et al., which are incorporated by reference as if fully set forth herein. In the methods described herein, however, squaric acid is used to modify surface characteristics such as the surface pKa and surface charge of microspheres.

In another embodiment, the methods described herein may be performed using oxocarbon acids. Oxocarbons of the general formula shown below, where R=Cl, alkyl, and aryl, were first reported by Cole, R. J. et al. *Science*, 1973, 179, 1324 and Schmidt, A. H., *Synthesis*, 1978, 1, which are incorporated by reference as if fully set forth herein.

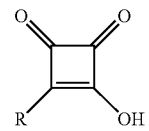

Using an appropriate linker group, R, the surface characteristics of microspheres can be modified with enolic acids that contain the general structure shown in Table 1, entry 1.

Vinyl containing monomers such as 3-hydroxy-4-(4-styryl)-3-cyclobutene-1,2-dione can be prepared by an extension of a general method reported in the literature by Meier, H. et al., *Tetrahedron Lett*. 1996, 37(8), 1191, which is incorporated by reference as if fully set forth herein. This functional monomer can be used to couple enolic acid groups to the surface of microspheres during polymerization. Vinyl enolic acids such as 3-hydroxy-4-vinyl-3-cyclobutene-1,2-dione have been reported by Sprenger, H. E. et al., *Angew.*

Chem. Int. Ed. Engl., 1968, 7, 530, which is incorporated by reference as if fully set forth herein.

In a different embodiment, the methods described herein may be performed using tropolones. For example, another enolic acid that may be used in the methods described herein as a surface modifier is 5-substituted hydroxy tropolone, which has the following chemical structure.

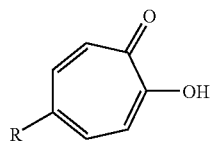

A modification of a method described by Uemura, T. et al., *Mol. Cryst. Liq. Cryst.* 1983, 95, 287, which is incorporated by reference as if fully set forth herein, can be used to produce 5-aminotropolone which can be attached to the surface of microspheres as shown below.

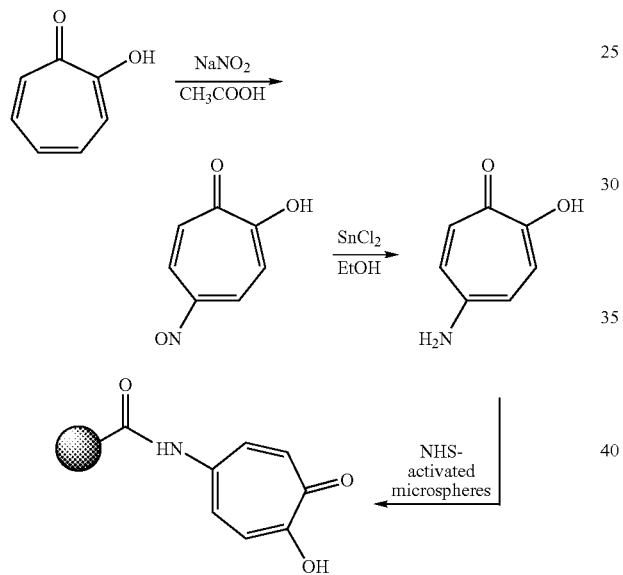

Procedures for the synthesis of various substituted tropolones have been reported for example, in *J. Chem. Soc. (C)* 1971, 878; *J. Chem. Soc. (PI)* 1976, 2329; *J. Chem. Soc.* 1951, 2352, which are incorporated by reference as if fully set forth herein. Synthesis of tropolones and microspheres with tropolone surface groups is described in Examples 4-6 provided below.

In further embodiments, other enolic acids that may be used in the methods described herein include cyanuric acid and its derivatives, boronic acid and its derivatives, silicic acids and their derivatives, and other enolic acids and their derivatives.

Cyanuric acid and derivatives thereof include compounds that can be represented by the general formula shown in Table 1, Entry 2. Resins activated with cyanuric chloride and resin bound triazine used to activate carboxyl groups for nucleophilic substitution at the carboxyl groups to produce amides are described by Venkataraman, K. et al., *Tetrahedron Lett.*, 1979, 32, 3037, which is incorporated by reference as if fully set forth herein Vinyl monomers of triazine such as that shown below may be used to couple cyanuric acid or its derivatives onto the surface of microspheres via incorporation during polymerization.

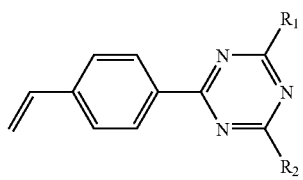

For example, vinyl monomers like the one shown above can be utilized for the preparation of microspheres with surface enolic acids including cyanuric acid and its derivatives. Similarly barbituric acid and its various derivatives can be incorporated either through polymerization or through a suitably functionalized linker (see, for example, Table 1, entry 3).

Other enolic acids and their derivatives that can be used in the method embodiments described herein include heterocyclic compounds represented by the general structures shown in Table 1, entries 5 and 6, which exhibit weak to moderate acidity and are available from various commercial sources. Enolic acids belonging to the family of ascorbic acids (see below) have a pKa of around 4.0-4.2.

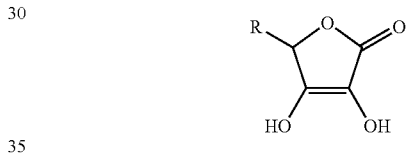

"Quinonoid" compounds (see Table 1, entry 7) such as chloranilic acid are also commercially available. With a suitable linker, these compounds can be immobilized on a microsphere surface. 2-Hydroxynaphthoquinone is a moderately strong acid and resembles oxocarbon acids. This compound has been described as a vinylog of semi-squaric acid. The hydroxy groups of 2-hydroxynaphthoquinone may be replaced by boronic acid, silic acid, selenic acid or phosphoric acid groups to alter the acidity of this compound and therefore the microsphere surface to which it is coupled.

Hydrazide derivatives such as Luminol (Table 1, entry 8) exhibit ionizable OH groups and can be immobilized on a microsphere surface using an amino group. Compounds like Luminol have been used for chemiluminescence analysis.

1,3-Cyclohexandione and its derivatives (Table 1, entry 9) possess pKa values around 4.8. Compounds like phenolenone are commercially available and with a suitable linker can be coupled to microspheres. The acidity of such compounds can be adjusted by introducing electron withdrawing and electron releasing groups including any such appropriate groups known in the art to such compounds.

The oxicam derivative "Mobic" is a member of the enolic acid group of nonsteroidal anti-inflammatory drugs. It has pKa values of 1.1 and 4.2. The high acidity of this compound is imparted by the presence of sulfone moieties in its structure. The incorporation of sulfones in conjugation with OH groups can be used to enhance the acidity of enolic acids (see Table 1, entries 10-13).

The structure shown in Table 1, entry 14 represents a class of acids that belongs to a general group classified as 'oxo' acids, which mimic the acidity of oxo carbon acids.

Examples of the most preferred vinyl monomers that can be polymerized with other monomers to yield microspheres having enolic acid containing surfaces are shown in Table 1, entry 15.

In additional embodiments, the methods described herein may be performed using "mixed enolic acids." For example, the availability of aniline and anisole squarates facilitates the immobilization of mixed enolic acids represented by the general structures shown in Table 1, entries 16-19. The syntheses of similar compounds are described by Gauger, J. et al., *Chem. Ber.*, 1970, 103, 2696, Bellus, D., *J. Am. Chem. Soc.*, 1978, 100, 8026, Law, K. Y. and Bailey, P. C., *J. Org. Chem.*, 1992, 57, 3278, and Meier, H. et al., *Tetrahedron Lett.*, 1996, 37, 1191, which are incorporated by reference as if fully set forth herein. Amino derivatized tropolone can be attached to oxocarbon acids such as squaric acid (Table 1, entry 19).

In addition, the methods described herein may be performed using "activated enolic acids." For example, any of the microspheres "coated with" enolic acids (i.e., having enolic acid molecules located on the microsphere surface) described herein can be activated to its enolic acid fluoride form using the procedure for converting squaric acid to squaric acid fluoride that is described in U.S. Patent Application Publication No. 2004/0039201 to Lugade et al. These new enolic acid fluorides could be used as crosslinkers in a manner similar to that in which the squaric acid fluoride groups are used as crosslinkers as described by Lugade et al. in this patent application.

By virtue of their bi-fuctional nature, enolic acid attached microspheres can also be used to form specific metal ion complexes (e.g. see below). Metal chelator complexes, in turn, can be used for site-specific capture of biomolecules and for affinity purification of proteins or peptides.

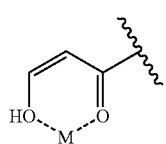

Table 1: Examples of Enolic Acids

The letter 'A' in the table represents any appropriate linker group known in the art that can be used to couple the enolic acid containing moiety to a microsphere (e.g., to a functional group located on the surface of the microsphere). The group 'A' may also contain a vinyl group to allow the enolic acid to be incorporated into a microsphere during polymerization of the polymer core of the microsphere.

Oxocarbon acids and Derivatives

1. 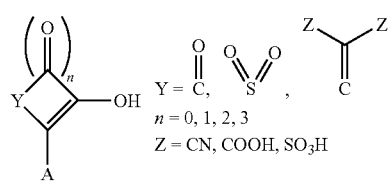

Cyanuric acid and derivatives

-continued

2. 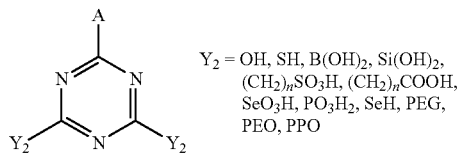

$Y_2$ = OH, SH, B(OH)$_2$, Si(OH)$_2$, (CH$_2$)$_n$SO$_3$H, (CH$_2$)$_n$COOH, SeO$_3$H, PO$_3$H$_2$, SeH, PEG, PEO, PPO

Barbituric acid and Derivatives

3. 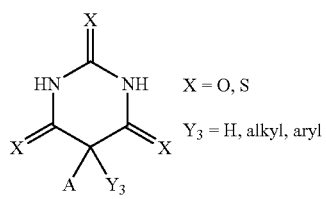

X = O, S $Y_3$ = H, alkyl, aryl

Tropolones, Benzotropolones and Derivatives

4. 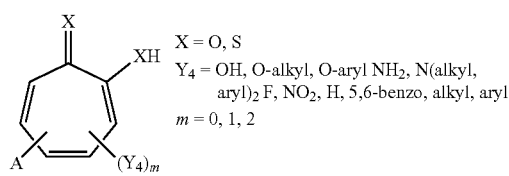

X = O, S $Y_4$ = OH, O-alkyl, O-aryl NH$_2$, N(alkyl, aryl)$_2$ F, NO$_2$, H, 5,6-benzo, alkyl, aryl m = 0, 1, 2

Heterocyclic

5. 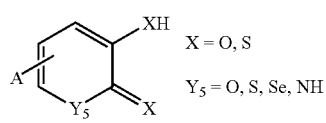

X = O, S $Y_5$ = O, S, Se, NH

Five membered rings/Ascorbic acid Type

6. 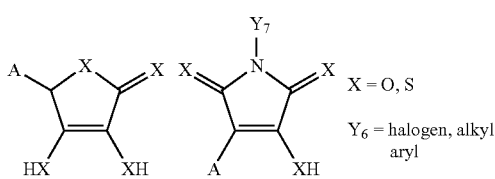

X = O, S $Y_6$ = halogen, alkyl aryl

Quinonoid Type

7. 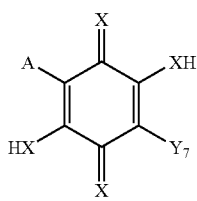

8. 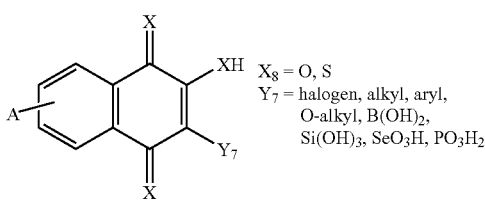

$X_8$ = O, S $Y_7$ = halogen, alkyl, aryl, O-alkyl, B(OH)$_2$, Si(OH)$_3$, SeO$_3$H, PO$_3$H$_2$ Luminol and Indophenol Type

| | | |
|---|---|---|
| 8. | 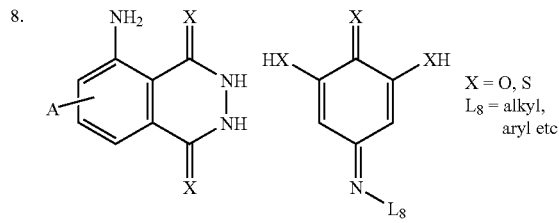 | X = O, S<br>L_8 = alkyl, aryl etc |
3-Hydroxy-enones or 1,3 diones
| | |
|---|---|
| 9. | 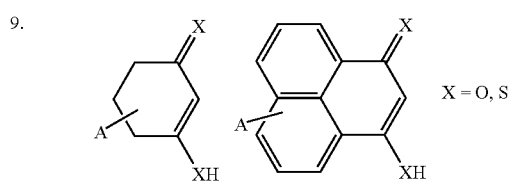 X = O, S |
Sulfones
| | | |
|---|---|---|
| 10. | 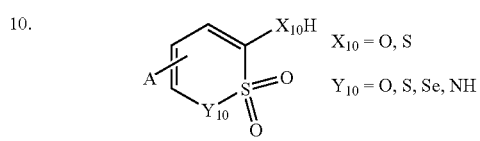 | $X_{10}$ = O, S<br>$Y_{10}$ = O, S, Se, NH |
| 11. | 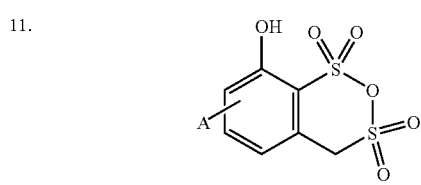 | |
| 12. | 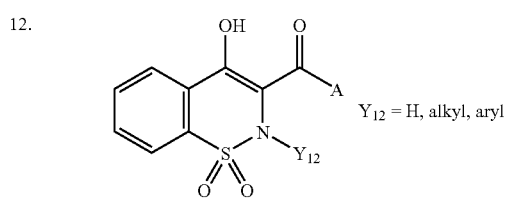 | $Y_{12}$ = H, alkyl, aryl |
| 13. | 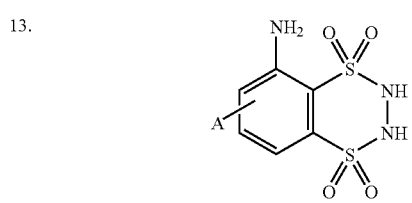 | |
Oxalic acid type
| | |
|---|---|
| 14. |  |
Vinyl Monomers
| | |
|---|---|
| 15. | 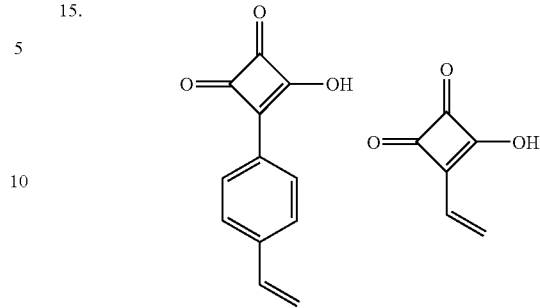 |
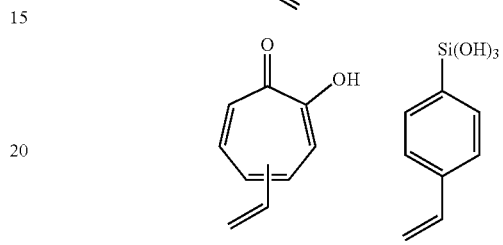
Mixed
| | | |
|---|---|---|
| 16. | 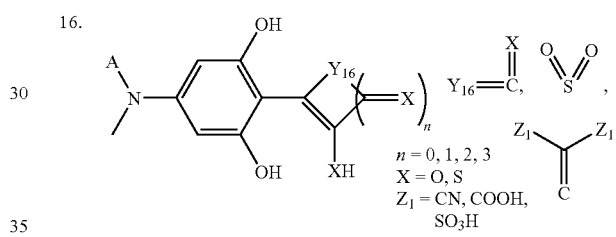 | n = 0, 1, 2, 3<br>X = O, S<br>$Z_1$ = CN, COOH, SO_3H |
| 17. | 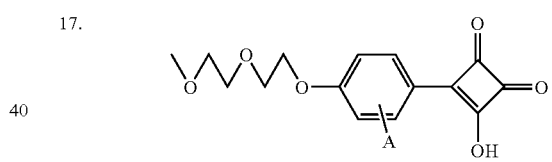 | |
| 18. | 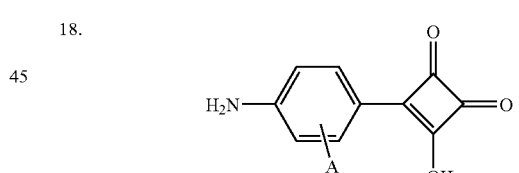 | |
| 19. | 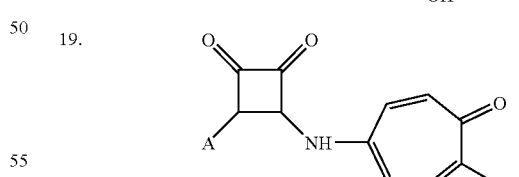 | |
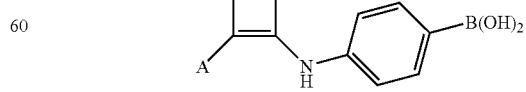
An example of a cyanuric acid derivative that can be used as a surface modifier and coupling activator for microspheres in the method embodiments described herein is given below.

The compound dimethoxy triazine methylmorpholine (DMTMM) was investigated as a surface modifier for microspheres. In the literature, DMTMM has been used as a peptide bond activation reagent. Alkyl substituted triazine derivatives are commercially available as DMTMM. DMTMM can also be synthesized as described in Examples 1 and 2 provided below. We explored its use as a surface modifier to which a reagent can be coupled for microspheres (see below).

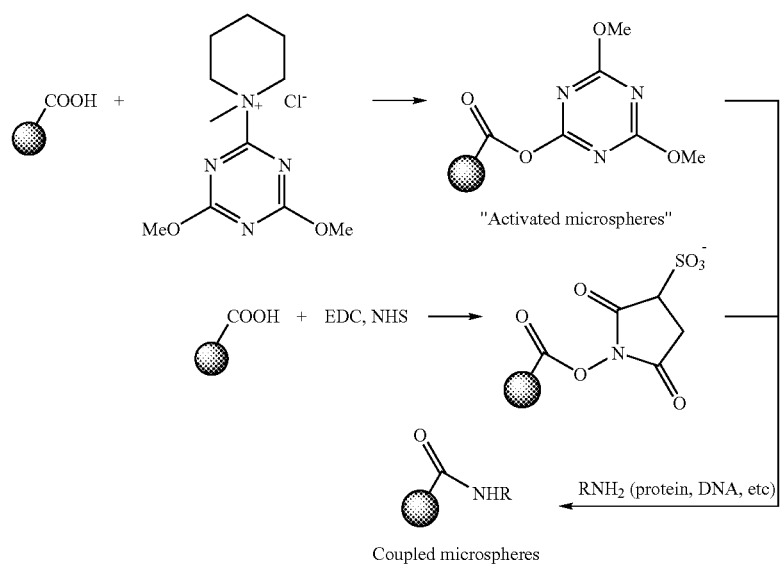

The coupling of DMTMM to microspheres performed well, but the microspheres coupled to DMTMM are more hydrophobic than microspheres activated with the commonly used surface modifier, sulfo-N-hydroxysuccinimide (sulfo-NHS). In other words, the DMTMM modified microspheres exhibited a propensity to stick to each other rather than dispersing in an aqueous solution. In contrast, microspheres with sulfo-NHS groups attached thereto retain a water-loving (i.e., hydrophilic) group (the sulfo) on the surface thereof when the sulfo-NHS is reacted with the original carboxyl group on the microspheres. The microspheres, therefore, stay well dispersed in water and aqueous solutions and solvents. In contrast, DMTMM is soluble in water because of the quaternary ammonium salt moiety that it contains. After reaction with a carboxyl group on the surface of a microsphere, this positive charge is lost along with the water solubility. In this manner, hydrophilic carboxyl groups on the surface of the microsphere are replaced with hydrophobic aromatic rings thereby reducing the hydrophilicity of the microspheres.

To increase the hydrophilicity of the activated microspheres, the methoxy groups of DMTMM were replaced with more hydrophilic chains as shown in the reaction below. Di-(polyethylene glycol) triazine chlorides have been prepared previously to introduce polyethylene glycol chains into biomolecules, as described in Japanese Patent No. 8092294 to Sakurai, et al. and reviewed by Roberts et al., *Adv. Drug Delivery Rev.*, 2002, 54, 459-476, which are incorporated by reference as if fully set forth herein. Other triazine compounds containing hydrophilic groups have been described by Pyzhov et al., Deposited Doc, 1982, VINITI 1408-82; Martin et al., *J. Prak. Chem.* 1981, 323, 694-699; Kashkin, et al.; *Zhurnal Organichkoi Khimii*, 1976, 12, 2030-2033; and Ahne et al., *Synthesis*, 1975, 184-186, which are incorporated by reference as if fully set forth herein. In one embodiment, therefore, the enolic acid used in the methods described herein includes DMTMM modified to contain hydrophilic groups. Hydrophilic groups such as quat-ammonium, sulfonate, phosphonate, polyethylene glycol (PEG) chains, dendrimeric structures, etc. could be used to increase the hydrophilicity of DMTMM and other surface modifiers subsequent to coupling of the surface modifiers to functional groups on the surface of the microsphere. The hydrophilic derivatives of DMTMM are used in the methods described herein as a replacement for EDC/NHS surface modifying and activating agents.

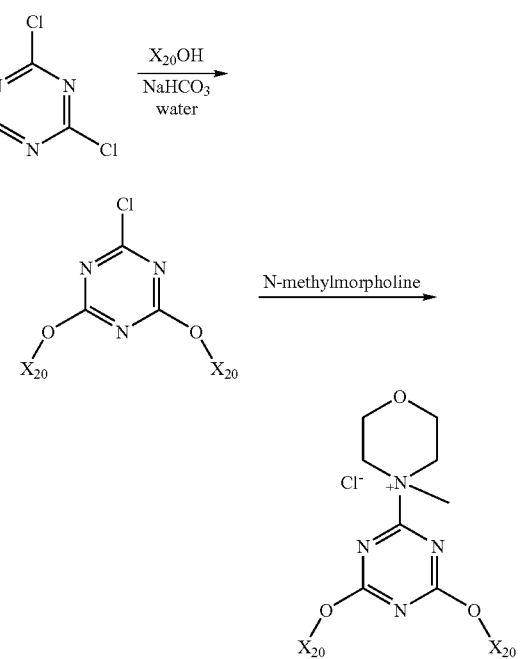

$X_{20}=$
—$(CH_2CH_2—O)_nCH_3$ n=1-100
—$(CH_2)_n—SO_3^-$
—$(CH_2)_n—PO_3^-$
—$(CH_2)_n—N(Y_{20})_3^+$, $(Y_{20}=H, Alkyl)$, n=1-3
—$Si(OCH_3)_2—(CH_2)_3—N(CH_3)_3^+$
—O-Dextran
—O-carbohydrate
—O-cellulose
—O-phosphatidyl choline One example of altering surface characteristics of (activating) microspheres with such a hydrophilic derivative is provided in Example 3 below.

Enolic acid containing surfaces of microspheres can be generated by two approaches. For example, a monomer may be obtained that contains both a vinyl group and an enolic acid group, and the monomer may be copolymerized with other monomers such as styrene to produce microspheres having enolic acid groups on the surface of the microspheres and thereby having the modified surface characteristics. The polymerization may be performed using any suitable method known in the art. Alternatively, coupling the enolic acid to the microsphere may include attaching the enolic acid to a surface of the microsphere. In other words, the surface of an already formed microsphere may be altered by attachment of the enolic acid. Attachment of an enolic acid to a formed microsphere may be performed as described herein or using any other suitable method known in the art.

In one embodiment, the enolic acid may include one or more enolic acid molecules coupled to different locations on the microsphere. In other words, two or more different enolic acids may be coupled to a microsphere. Molecules of each of the different enolic acids may be coupled directly to functional groups present on the microsphere surface. Alternatively, monomers containing different enolic acids may be copolymerized possibly in combination with other monomers to form the polymer core of the microsphere having the enolic acids located on a surface thereof.

In one embodiment, the modified surface characteristics increase a stability of the reagent when the reagent is coupled to the microsphere. In another embodiment, the modified surface characteristics improve performance of an assay carried out with the microsphere. For example, different biomolecules may require different surface environments (i.e., the environment proximate to the surface of the microsphere) for optimal assay performance (e.g., for optimal binding to or reaction with an analyte in a sample). These local environments can be created and adjusted using the proposed surface groups. Some of the surface modifiers described herein will increase reagent stability or improve assay performance. Other surface modifiers described herein allow for easier attachment of the biomolecules to the microsphere surface.

For example, the DMTMM based surface modifier described above may be used to reduce inconsistent coupling of biological material to the surface of microspheres. In this manner, the surface modifier may not necessarily be used to form a "self-coupling" microsphere (i.e., a microsphere having surface groups that selectively and spontaneously couple to a reagent), but the surface modifier may be used to replace the EDC/sulfo-NHS cross-linking pair currently used to provide a microsphere having an improved surface modifier attached thereto and improved surface characteristics.

In addition, in some instances, standard EDC/sulfo-NHS coupling procedures may be somewhat problematic. For example, EDC and sulfo-NHS are hygroscopic solids that react with moisture in the air, and special precautions must be used to keep the surface modifier in the bottle fresh. Working solutions of the surface modifiers must be made immediately before use. The urea side products from EDC activation are sometimes hard to remove from the bead suspension and can interfere with subsequent coupling reactions or assays.

The methods described herein provide a number of advantages over standard methods for coupling reagents to microspheres. For example, DMTMM type cross-linkers can be used alone to activate microspheres (instead of using two surface modifiers). In addition, aqueous solutions of DMTMM are stable for several hours at room temperature and much longer if kept frozen. Furthermore, DMTMM crystals are more stable to moisture in the air and so are easier to work with successfully. Moreover, the synthesis of DMTMM is less complicated than that for EDC, which may increase the quality and consistency of the surface modifier.

Another embodiment relates to a microsphere that includes an enolic acid coupled to a polymer core of the microsphere such that the enolic acid modifies surface characteristics of the microsphere. The polymer core of the microsphere may be formed of any suitable polymer known in the art. The enolic acid may include one or more enolic acid molecules coupled to different locations on the microsphere. A reagent can be coupled to the microsphere via the enolic acid. In other embodiments, the enolic acid may be replaced with an enolic acid derivative or a mixed functional group. In further embodiments, the enolic acid may be more generally represented as an ionizable polar group that is in conjugation with a chemical group. The chemical group may include a sulfone group or a carbonyl group.

In one embodiment, the enolic acid contains at least one hydrophilic group. In another embodiment, the enolic acid may include a deltic, squaric, croconic, or rhodizonic acid or other homolog. In a different embodiment, the enolic acid may include 5-substituted hydroxy tropolone. In other embodiments, the enolic acid may include a cyanuric acid or a cyanuric acid derivative. In a further embodiment, the enolic acid may include DMTMM modified to contain hydrophilic groups. In alternative embodiments, the enolic acid may include a mixed functional group. The mixed functional group may include a boronic acid or a boronic acid derivative. In different embodiments, the enolic acid may include a silicic acid or a silicic acid derivative.

In one embodiment, the enolic acid may be coupled to the polymer core via copolymerization using a monomer containing a vinyl group and the enolic acid with a different monomer. In a different embodiment, the enolic acid may be coupled to the polymer core via attachment of the enolic acid to a surface of the polymer core.

The modified surface characteristics may increase a stability of the reagent when the reagent is coupled to the microsphere. The modified surface characteristics may also improve performance of an assay carried out with the microsphere. The reagent may be a biomolecule. The surface characteristics may include charge density. In addition, the surface characteristics may include pKa. Each of the embodiments of the microsphere may be further configured, composed, and/or formed as described herein. Each of the embodiments of the microsphere described above has all of the advantages of the methods described above.

Microspheres having a surface modifier described herein attached thereto can be supplied as "ready to use" microspheres. In addition, one or more surface modifiers can be supplied as a separate kit to activate surface groups on (couple to surface groups on) the microspheres.

In one embodiment, the kit includes microspheres. The kit also includes an activating reagent containing one or more surface modifiers such as an enolic acid. In addition, the kit includes one or more chemicals, one or more devices, or some combination thereof that can be used to couple the enolic acid to a polymer core of the microsphere (or groups on the surface of the polymer core of the microsphere) such that the enolic acid modifies surface characteristics of the microspheres. One or more reagents can be coupled to the microspheres via the enolic acid. The reagent(s) may or may not be included in the kit.

The kit and these elements of the kit may be further configured as described herein. For example, in some embodiments, the enolic acid may be replaced with an enolic acid derivative or a mixed functional group. In further embodiments, the enolic acid may be more generally represented as an ionizable polar group that is in conjugation with a chemical group. The chemical group may include, for example, a sulfone group or a carbonyl group. Each of the embodiments of the kit described herein has all of the advantages of the methods described above.

The following examples are not to be considered limiting embodiments of the invention and are included herein for example purposes only.

The procedures in Examples 1 and 2 are based on the synthesis of DMTMM described by Kunishima, M. et al., *Tetrahedron Lett.*, 40, 5327-5330, 1999, and Cronin, J. S. et al., *Syn. Commun.*, 26 (18), 3491-3494, 1996, which are incorporated by reference as if fully set forth herein.

EXAMPLE 1

Synthesis of
2-chloro-4,6-di-(2-methoxyethoxy)-1,3,5-triazine

To 14.43 g (190 mmole) of 2-methoxy ethanol, 6.83 g (81 mmole) of sodium bicarbonate, and 1.3 mL (70 mmole) of deionized water at room temperature was added 5.0 g (27 mmole) of cyanuric chloride. The temperature of the solution was raised to 30° C. and stirred for 1 hour at which time the evolution of carbon dioxide ceased. The temperature of the solution was raised to 45° C. and stirring was continued overnight. After cooling, the mixture was filtered, and the solids rinsed with methylene chloride. The combined filtrates were concentrated in vacuo to 8 g of 2-chloro-4,6-di-(2-methoxyethoxy)-1,3,5-triazine as a milky liquid which solidified to a waxy solid in the freezer (−18° C.).

Proton nuclear magnetic resonance ($^1$H NMR) of the product produced the following results: (CDCl$_3$, 60 MHz) δ 4.7-4.4 (m, 4 Hz), 3.8-3.5 (m, 4 Hz), 3.4 (s, 6 Hz). Infrared (IR) spectroscopy of the product (neat) found the following characteristic IR absorption frequencies: 1557 cm$^{-1}$, 1417 cm$^{-1}$, 1330 cm$^{-1}$, 1115 cm$^{-1}$, 1050 cm$^{-1}$, 1022 cm$^{-1}$, and 814 cm$^{-1}$.

EXAMPLE 2

Synthesis of 2-chloro-4,6-di-(2-(diisopropylamino) ethoxy)-1,3,5-triazine

To 27.6 g (190 mmole) of 2-(diisopropylamino)ethanol, 6.83 g (81 mmole) of sodium bicarbonate, and 1.3 mL (70 mmole) of deionized water at room temperature was added 5.0 g (27 mmole) of cyanuric chloride. The temperature of the solution was raised to 30° C. and stirred for 1 hour at which time the evolution of carbon dioxide ceased. The temperature of the solution was raised to 45° C. and stirring was continued overnight. After cooling, the mixture was filtered, and the solids rinsed with methylene chloride. The combined filtrates were concentrated in vacuo to 6 g of 2-chloro-4,6-di-(2-(diisopropylamino)ethoxy)-1,3,5-triazine as a liquid.

EXAMPLE 3

Synthesis of 4-(4,6-di-(2-methoxyethoxy)-1,3,5-triazin-2-yl)-4-methylmorpholinium chloride To 1.05 g (4 mmole) of 2-chloro-4,6-di-(2-methoxyethoxy)-1,3,5-triazine (obtained as described in Example 1) in 3.5 mL of dry tetrahydrofuran was added 530 µL of N-methyl morpholine. The solution was stirred for 30 minutes, filtered, and dried in an Abderhalden apparatus using acetone for 12 hours to yield 0.5 g (34%) of 4-(4,6-di-(2-methoxyethoxy)-1,3,5-triazin-2-yl)-4-methylmorpholinium chloride as a white powder. IR spectroscopy of the product (neat) identified the following characteristic IR absorption frequencies: 1605 cm$^{-1}$, 1417 cm$^{-1}$, 1336 cm$^{-1}$, 1300 cm$^{-1}$, 1118 cm$^{-1}$, 1094 cm$^{-1}$, 1068 cm$^{-1}$, 1053 cm$^{-1}$, 1028 cm$^{-1}$, 1009 cm$^{-1}$, 991 cm$^{-1}$, 972 cm$^{-1}$, 858 cm$^{-1}$, and 821 cm$^{-1}$.

4-(4,6-di-(2-diisopropylamino)ethoxy)-1,3,5-triazin-2-yl)-4-methylmorpholinium chloride was produced in a similar manner from the chloride obtained in Example 2.

EXAMPLE 4

General Procedure for the Activation of Carboxylated Microspheres with Hydrophilic DMTMM Derivatives To an aliquot of 5.0E6 carboxylated microspheres suspended in 90 µL of an appropriate, non-nucleophilic buffer (pH 5-9) was added 10 µL of a 50 mg/mL solution of one of the newly described hydrophilic DMTMM derivatives (e.g., one of the compounds as described in Example 3) in the same buffer. The suspension was agitated for 20-60 minutes. The excess reagent could be separated from the microspheres by any convenient method known to the art (e.g. repeated centrifugation and decantation). The activated microspheres will now react spontaneously with amine containing molecules (e.g. protein) in about 2 hours in an appropriate, non-nucleophilic buffer (pH 4-9).

EXAMPLE 5

Synthesis of 5-nitroso tropolone

To a stirred solution of 2.05 g (16.9 mmole) of tropolone in 6 mL of deionized water and 6 mL of glacial acetic acid was added dropwise a solution of 1.25 g (18.1 mmole) of sodium nitrite in 5 mL of deionized water. After an additional 1 hour of stirring, the resulting solids were filtered and dried in vacuo for 2 hours to give 5-nitroso-tropolone as a yellow solid. IR spectroscopy of the product (neat) found the following characteristic IR absorption frequencies: 1603 cm$^{-1}$, 1519 cm$^{-1}$, 1316 cm$^{-1}$, 1110 cm$^{-1}$, 1015 cm$^{-1}$, 845 cm$^{-1}$, 812 cm$^{-1}$, and 781 cm$^{-1}$.

EXAMPLE 6

Synthesis of 5-aminotropolone

To a stirred solution of 0.39 g of 5-nitrosotropolone (2.6 mmole, obtained from the previous example) and 10 mL of absolute ethanol was added 2.92 g of Tin (II) chloride (12.9 mmole). After 40 minutes at reflux the solution was cooled, filtered, and the liquefied portion was partitioned between ethyl acetate and water. The organic fraction was concentrated in vacuo to give 35 mg (10%) of 5-aminotropolone as a yellow solid. IR spectroscopy of the product (neat) found the following characteristic IR absorption frequencies: 3319 cm$^{-1}$, 3181 cm$^{-1}$, 2925 cm$^{-1}$, 1511 cm$^{-1}$, 1410 cm$^{-1}$, 1261 cm$^{-1}$, 837 cm$^{-1}$, 781 cm$^{-1}$, and 739 cm$^{-1}$.

EXAMPLE 7

Synthesis of Microspheres with Tropolone Surface Groups

To 100E6 carboxylated microspheres (previously activated with sulfo-N-hydroxysuccinimide and EDC) in 0.5 mL of carbonate buffer (pH 9) was added 2 mg of 5-aminotropolone dissolved in 25 µL of dimethyl sulfoxide. The suspension was agitated for 4 hours, and the excess reagent was washed away from the microspheres.

Turning now to the drawings, FIG. 1 illustrates one example of a measurement system that may be used to perform experiments with embodiments of the microspheres described herein. It is noted that FIG. 1 is not drawn to scale. In particular, the scale of some of the elements of the figure is greatly exaggerated to emphasize characteristics of the elements. Some elements of the measurement system such as a digital signal processor (DSP) have not been included in the figure for the sake of clarity.

In FIG. 1, the measurement system is shown along a plane through the cross-section of cuvette 12 through which microspheres 10 flow. In one example, the cuvette may be a standard quartz cuvette such as that used in standard flow cytometers. Any other suitable type of viewing or delivery chamber, however, may also be used to deliver the sample for analysis. Microspheres 10 may be formed according to the embodiments described herein.

The measurement system includes light source 14. Light source 14 may include any appropriate light source known in the art such as a laser. The light source may be configured to emit light having one or more wavelengths such as blue light or green light. Light source 14 may be configured to illuminate the microspheres as they flow through the cuvette. The illumination may cause the microspheres to emit fluorescent light having one or more wavelengths or wavelength bands. In some embodiments, the system may include one or more lenses (not shown) configured to focus light from the light source onto the microspheres or the flowpath. The system may also include more than one light source. In one embodiment, the light sources may be configured to illuminate the microspheres with light having different wavelengths (e.g., blue light and green light). In some embodiments, the light sources may be configured to illuminate the microspheres at different directions.

Light scattered forwardly from the microspheres may be directed to detection system 16 by folding mirror 18 or another such light directing component. Alternatively, detection system 16 may be placed directly in the path of the forwardly scattered light. In this manner, the folding mirror or other light directing components may not be included in the system. In one embodiment, the forwardly scattered light may be light scattered by the microspheres at an angle of about 180 degrees from the direction of illumination by light source 14, as shown in FIG. 1. The angle of the forwardly scattered light may not be exactly 180 degrees from the direction of illumination by the light source such that incident light from the light source may not impinge upon the photosensitive surface of the detection system. For example, the forwardly scattered light may be light scattered by the microspheres at angles less than or greater than 180 degrees from the direction of illumination (e.g., light scattered at an angle of about 170 degrees, about 175 degrees, about 185 degrees, or about 190 degrees).

Light scattered and/or emitted by the microspheres at an angle of about 90 degrees from the direction of illumination by the light source may also be collected. In one embodiment, this scattered light may be separated into more than one beam of light by one or more beamsplitters or dichroic mirrors. For example, light scattered at an angle of about 90 degrees to the direction of illumination may be separated into two different beams of light by beamsplitter 20. The two different beams of light may be separated again by beamsplitters 22 and 24 to produce four different beams of light. Each of the beams of light may be directed to a different detection system, which may include one or more detectors. For example, one of the four beams of light may be directed to detection system 26. Detection system 26 may be configured to detect light scattered by the microspheres.

The other three beams of light may be directed to detection systems 28, 30, and 32. Detection systems 28, 30, and 32 may be configured to detect fluorescence emitted by the microspheres. Each of the detection systems may be configured to detect fluorescence of a different wavelength or a different range of wavelengths. For example, one of the detection systems may be configured to detect green fluorescence. Another of the detection systems may be configured to detect yellow-orange fluorescence, and the other detection system may be configured to detect red fluorescence.

In some embodiments, spectral filters 34, 36, and 38 may be coupled to detection systems 28, 30, and 32, respectively. The spectral filters may be configured to block fluorescence of wavelengths other than that which the detection systems are configured to detect. In addition, one or more lenses (not shown) may be optically coupled to each of the detection systems. The lenses may be configured to focus the scattered light or emitted fluorescence onto a photosensitive surface of the detectors.

The detector's output current is proportional to the fluorescent light impinging on it and results in a current pulse. The current pulse may be converted to a voltage pulse, low pass filtered, and then digitized by an A/D converter. A DSP integrates the area under the pulse to provide a number which represents the magnitude of the fluorescence.

In some embodiments, the output signals generated from fluorescence emitted by the microspheres may be processed to determine an identity of the microspheres and information about a reaction taken or taking place on the surface of the microspheres. For example, two of the output signals may be used to determine an identity of the microspheres, and the other output signals may be used to determine a reaction taken or taking place on the surface of the microspheres. The identity of the microspheres may be determined based on a ratio of the output signals generated in two or more different detection windows. For example, if detection systems 30 and 32 have different detection windows, the identity of the microspheres may be determined from a ratio of output signals generated by detection system 30 to output signals generated by detection system 32, coupled with the intensity of each signal. Therefore, the selection of the detectors and the spectral filters may vary depending on the type of dyes incorporated into or bound to the microspheres and/or the reaction being measured (i.e., the dye(s) incorporated into or bound to the reactants involved in the reaction).

Although the system of FIG. 1 is shown to include two detection systems having two different detection windows for distinguishing between microspheres having different dye characteristics, it is to be understood that the system may include more than two such detection windows (i.e., 3 detection windows, 4 detection windows, etc.). In such embodiments, the system may include additional beamsplitters and additional detection systems having other detection windows. The detection windows for more than two detection systems may be determined as described above. In addition, spectral filters and/or lenses may be coupled to each of the additional detection systems.

In another embodiment, the system may include two or more detection systems configured to distinguish between different materials that are reacted on the surface of the microspheres. The different reactant materials may have dye characteristics that are different than the dye characteristics of the microspheres.

Additional examples of measurement systems that may be used to perform measurements on the surface modified microspheres described herein are illustrated in U.S. Pat. No. 5,981,180 to Chandler et al., U.S. Pat. No. 6,046,807 to Chandler, U.S. Pat. No. 6,139,800 to Chandler, U.S. Pat. No. 6,366,354 B1 to Chandler, U.S. Pat. No. 6,411,904 B1 to Chandler, U.S. Pat. No. 6,449,562 B1 to Chandler et al., and U.S. Pat. No. 6,524,793 B1 to Chandler et al., which are incorporated by reference as if fully set forth herein. The measurement system described herein may also be further configured as described in these patents. In addition, the assays and experiments in which the microsphere embodiments described herein may be used include any of the assays and experiments described in these patents and any other assays and experiments known in the art.

It will be appreciated to those skilled in the art having the benefit of this disclosure that this invention is believed to provide methods for altering surface characteristics of a microsphere. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for altering surface characteristics of a microsphere, comprising;
    coupling an enolic acid derivative of dimethoxy triazine methylmorpholine modified to contain hydrophilic groups to the microsphere to modify surface characteristics of the microsphere; and
    subsequently coupling a reagent to the microsphere, wherein the reagent is a molecule which is reactive with an analyte of an assay.

2. The method of claim 1, wherein said coupling comprises copolymerizing a monomer containing a vinyl group and the enolic acid derivative with a different monomer to form the microsphere having the modified surface characteristics.

3. The method of claim 1, wherein said coupling comprises attaching the enolic acid derivative to a functional group which is attached to a surface of the microsphere.

4. The method of claim 1, wherein the modified surface characteristics increase a stability of the reagent when the reagent is coupled to the microsphere.

5. The method of claim 1, wherein the modified surface characteristics improve performance of an assay carried out with the microsphere.

6. The method of claim 1, wherein the reagent comprises a biomolecule.

7. The method of claim 1, wherein the step of coupling comprises coupling additional enolic acid derivative molecules of dimethoxy triazine methylmorpholine modified to contain hydrophilic groups to different locations on the microsphere.

8. The method of claim 1, wherein the surface characteristics comprise charge density.

9. The method of claim 1, wherein the surface characteristics comprise pKa.

10. A microsphere, comprising;
    an enolic acid derivative of dimethoxy triazine methylmorpholine modified to contain hydrophilic groups, wherein the modified enolic acid derivative is coupled to the microsphere for modifying surface characteristics of the microsphere; and
    a reagent coupled to the microsphere via displacement of the modified enolic acid derivative, wherein the reagent is a molecule which is reactive with an analyte of an assay.

11. The microsphere of claim 10, wherein the modified enolic acid derivative is directly attached to a core material of the microsphere.

12. The microsphere of claim 10, wherein the modified enolic acid derivative is attached to a functional group which is coupled to a core material of the microsphere.

13. The microsphere of claim 10, wherein the modified enolic acid derivative is ionized to generate surface characteristics which increase a stability of the reagent.

14. The microsphere of claim 10, wherein the modified enolic acid derivative is ionized to generate surface characteristics which improve performance of an assay carried out with the microsphere.

15. The microsphere of claim 10, wherein the reagent comprises a biomolecule.

16. The microsphere of claim 10, further comprising additional enolic acid derivative molecules of dimethoxy triazine methylmorpholine modified to contain hydrophilic groups coupled to different locations on the microsphere.

17. The microsphere of claim 10, wherein the surface characteristics comprise charge density.

18. The microsphere of claim 10, wherein the surface characteristics comprise pKa.

19. The method of claim 1, further comprising disposing the microsphere in a solution having a pH between approximately 5.0 and approximately 9.0 prior to the step of coupling the reagent to the microsphere.

20. The microsphere of claim 10, wherein the enolic acid derivative comprises a derivative of dimethoxy triazine methylmorpholine in which one or more methoxy groups of dimethoxy triazine methylmorpholine are replaced to include a quaternary ammonium chain, a sulfonate chain, a phosphonate chain, a polyethylene glycol chain, or a dendrimeric structure.

* * * * *

UNITED STATES PATENT AND TRADEMARK OFFICE
CERTIFICATE OF CORRECTION

PATENT NO.        : 7,867,774 B2                                                    Page 1 of 1
APPLICATION NO.   : 11/247943
DATED             : January 11, 2011
INVENTOR(S)       : Ananda G. Lugade et al.

It is certified that error appears in the above-identified patent and that said Letters Patent is hereby corrected as shown below:

In column 15, lines 10-33, delete chemical drawing:

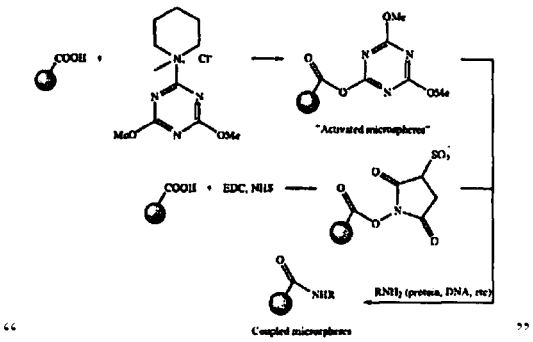

and insert

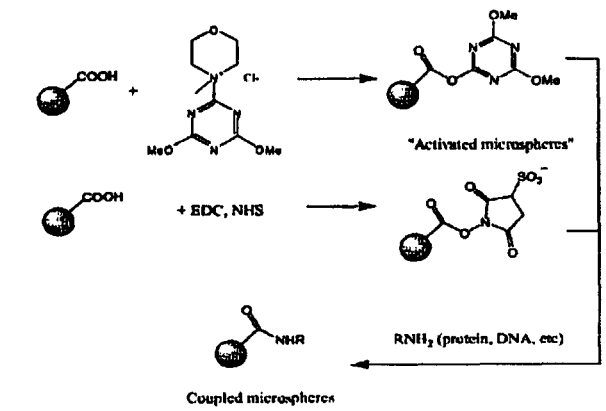

-- therefor.

Signed and Sealed this
Eighteenth Day of October, 2011

David J. Kappos
*Director of the United States Patent and Trademark Office*

UNITED STATES PATENT AND TRADEMARK OFFICE
CERTIFICATE OF CORRECTION

PATENT NO. : 7,867,774 B2  
APPLICATION NO. : 11/247943  
DATED : January 11, 2011  
INVENTOR(S) : Lugade et al.

Page 1 of 1

It is certified that error appears in the above-identified patent and that said Letters Patent is hereby corrected as shown below:

In the Claims:

In claim 1, column 23, line 55, delete "of" and insert --, wherein the enolic acid derivative is a-- therefor.

In claim 7, column 24, line 14, delete "of dimethoxy triazine methylmorpholine" and insert --, wherein the enolic acid derivative molecules are dimethoxy triazine methylmorpholine molecules-- therefor.

In claim 10, column 24, line 22, delete "of" and insert --, wherein the enolic acid derivative is a-- therefor.

In claim 16, column 24, line 47, delete "of dimethoxy triazine methylmorpholine" and insert --, wherein the enolic acid derivative molecules are dimethoxy triazine methylmorpholine molecules-- therefor.

Signed and Sealed this  
Fourth Day of June, 2013

Teresa Stanek Rea  
*Acting Director of the United States Patent and Trademark Office*